United States Patent [19]
Lauff et al.

[11] Patent Number: 5,252,483
[45] Date of Patent: Oct. 12, 1993

[54] DEGRADATION OF FERRIC CHELATES BY A PURE CULTURE OF AGROBACTERIUM SP.

[75] Inventors: John Lauff; James Breitfeller, both of Rochester, N.Y.; D. Bernie Steele, Auburn, Ala.; Louise Coogan, Hilton, N.Y.

[73] Assignee: Genencor International, Inc., Rochester, N.Y.

[21] Appl. No.: 603,381

[22] Filed: Oct. 26, 1990

Related U.S. Application Data

[63] Continuation-in-part of Ser. No. 507,931, Apr. 11, 1990, abandoned.

[51] Int. Cl.⁵ .............. C12S 1/00; B09B 3/00; C12N 1/20; C12P 3/00
[52] U.S. Cl. ............... 435/262; 435/262.5; 435/252.2; 435/168; 210/611
[58] Field of Search ........... 435/262.5, 262, 252.2, 435/168; 210/611

[56] References Cited

U.S. PATENT DOCUMENTS 4,634,667  1/1987  Linton et al. ............ 435/101
4,673,644  6/1987  Harad et al. ............ 435/101

FOREIGN PATENT DOCUMENTS 58-43782  9/1981  Japan .
525627  5/1974  U.S.S.R. .

OTHER PUBLICATIONS

Bergy's Manual of Determinative Bacteriology, 8th, pp. 264–265, 1974.
Gerike et al, Ecotoxicology and Env. Safety, 3:159–173 (1975).
Tom et al, Proc. Roy. Soc. of London, 189:347–357 (1975).
Tiedje, Appl. Microbiol., 39:327–329 (1975).
Tiedje, J. Environ. Qual., 6:21–26 (1977).
Belly et al, Appl. Microbiol., 29:787–794 (1975).
Lockhart et al, Env. Sci. and Technol., 9:1035–1038 (1975).
Lockhart et al, Environ. Lett., 9:19–31 (1975).
Drucker, Methods in Microbiology, vol. 9, J. R. Norris, Ed. Academic Press, London, pp. 51–125.
Standard Methods For The Examination of Water and Waste Water, American Public Health Assoc., Washington, D.C. 16th Ed., pp. 532–538, (1985).
Stookey, Anal. Chem., 42:779–781 (1970).
Egli, Microbiological Sciences, 5(2):36–41 (1988).
Hill-Cottingham, Nature, 175(4451): 347–348 (Feb. 19, 1955).
Hofer, Bacterium Radio-Bacter Lohnis, pp. 193–224. (1939).
Lambert et al, Inorganic Chemistry, 2(1): 127–129 (Feb. 1963).
Lippincott et al, The Genus Agrobacterium, chapter 68, pp. 842–855.
Means et al, Science, 200: 1477–1481 (Jun. 1978).
Neilands, Ann. Rev. Microbiol., 36: 285–309 (1982).
Wagegg et al, Journal of Bacteriology, 145(1): 156–163 (Jan. 1981).

*Primary Examiner*—Michael G. Wityshyn
*Assistant Examiner*—Timothy J. Reardon
*Attorney, Agent, or Firm*—Margaret A. Horn

[57] ABSTRACT

A novel microorganism has been isolated and identified as *Agrobacterium sp.*, a gram-negative aerobe. The *Agrobacterium sp.* microorganisms has been found to efficiently degrade ferric chelates of aminopolycarboxylic acids, such as ethylenediaminetetraacetic acid and related compounds, found in aqueous waste solutions. A biologically pure culture of *Agrobacterium sp.* and a process for using the culture are disclosed.

12 Claims, 6 Drawing Sheets

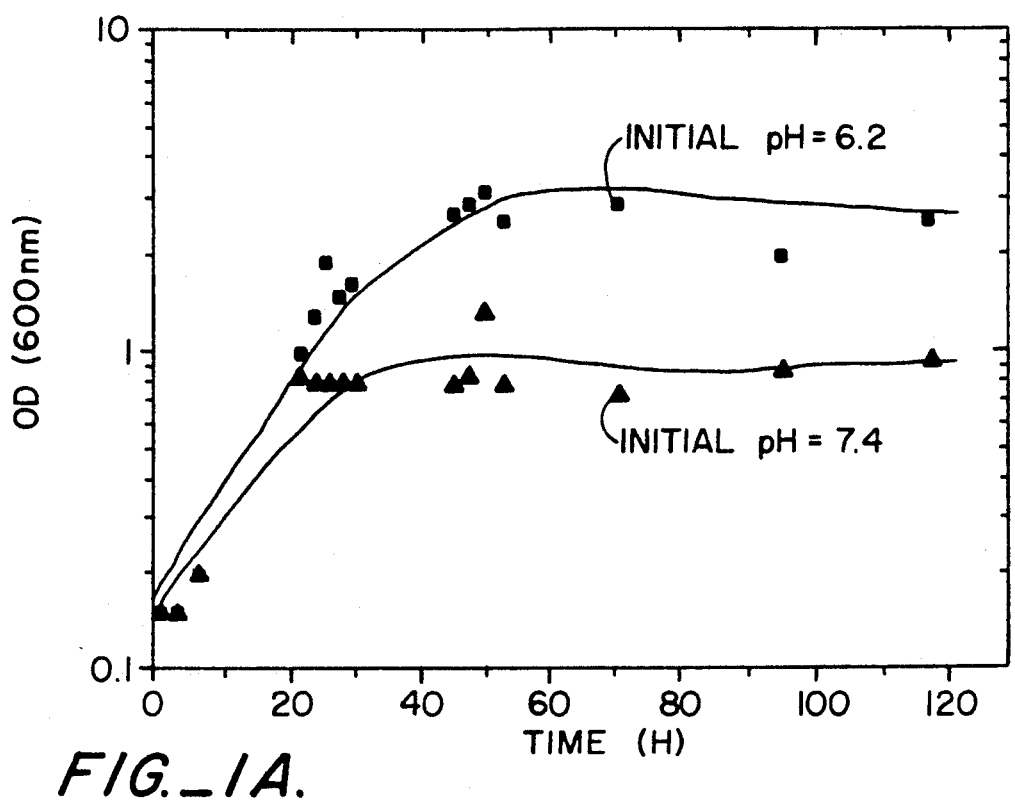
FIG._1A.
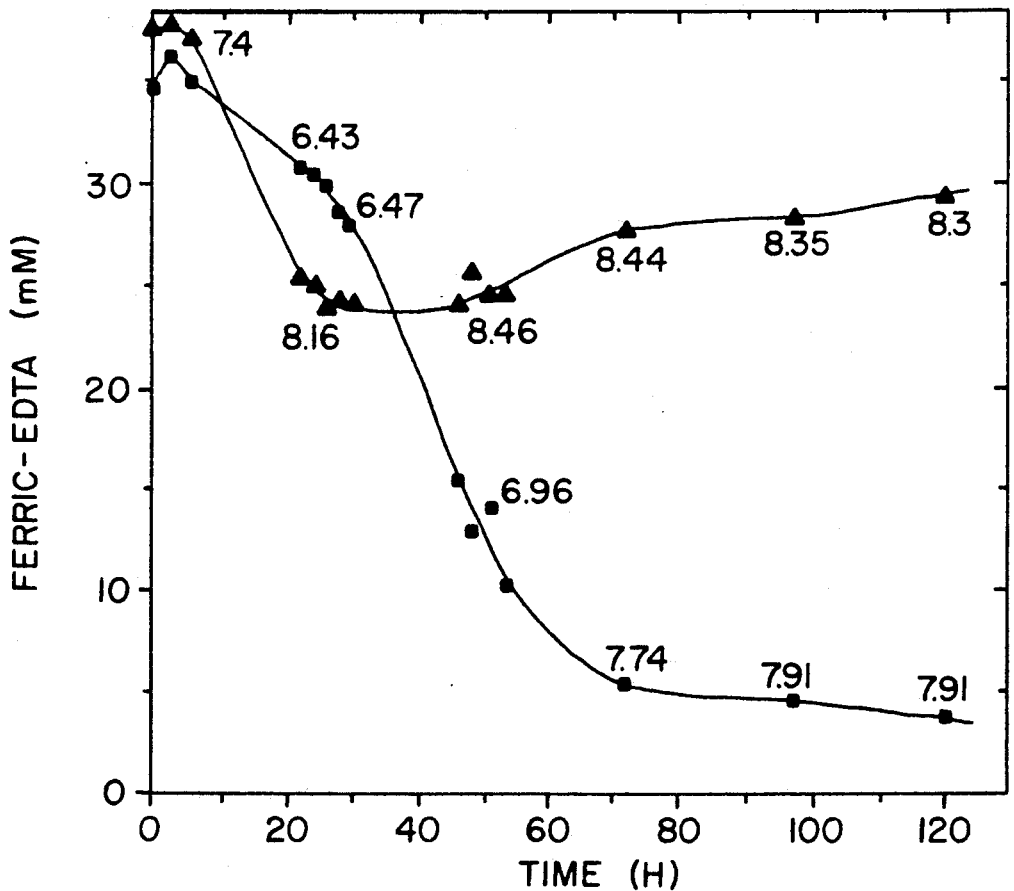
FIG._1B.

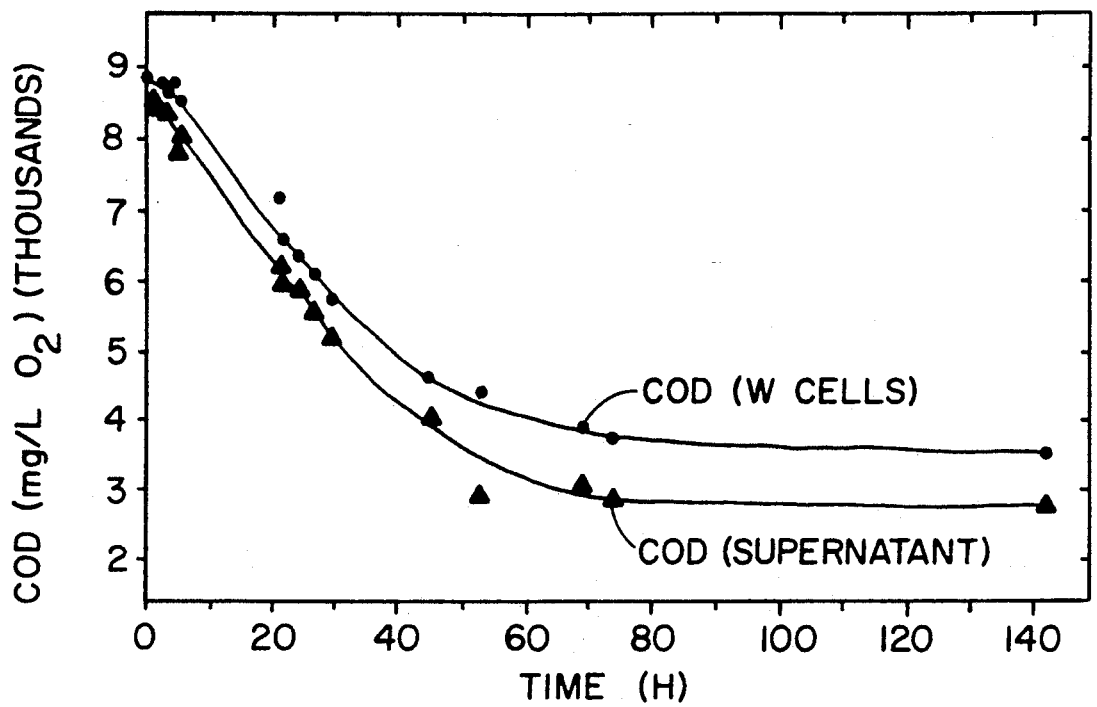
FIG._2A.
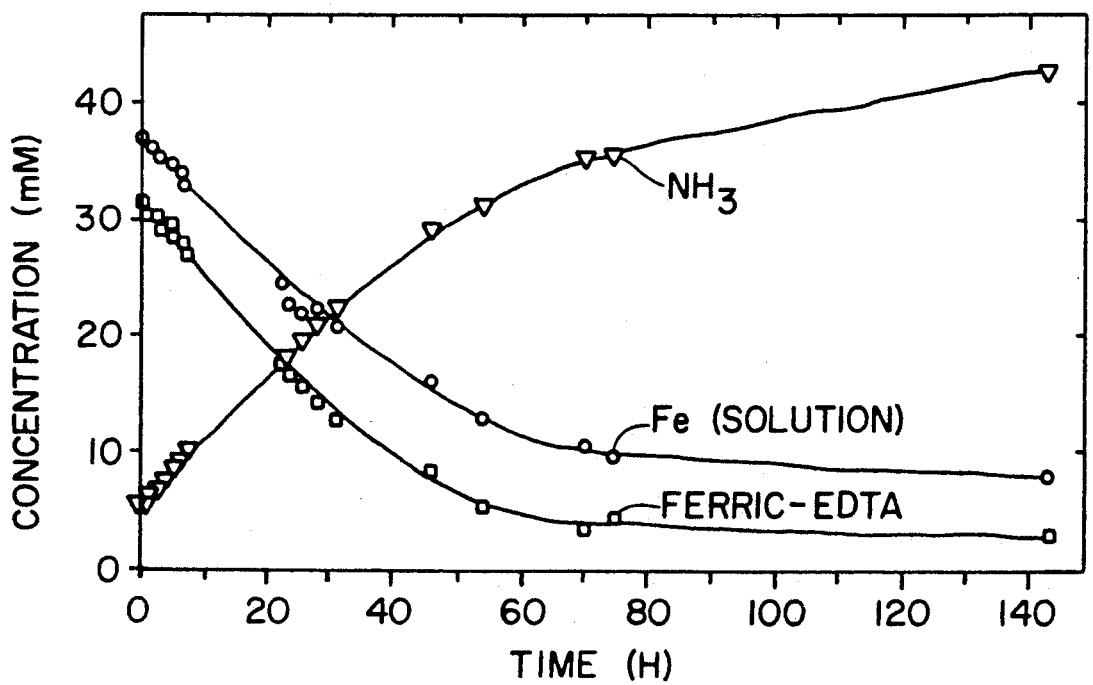
FIG._2B.

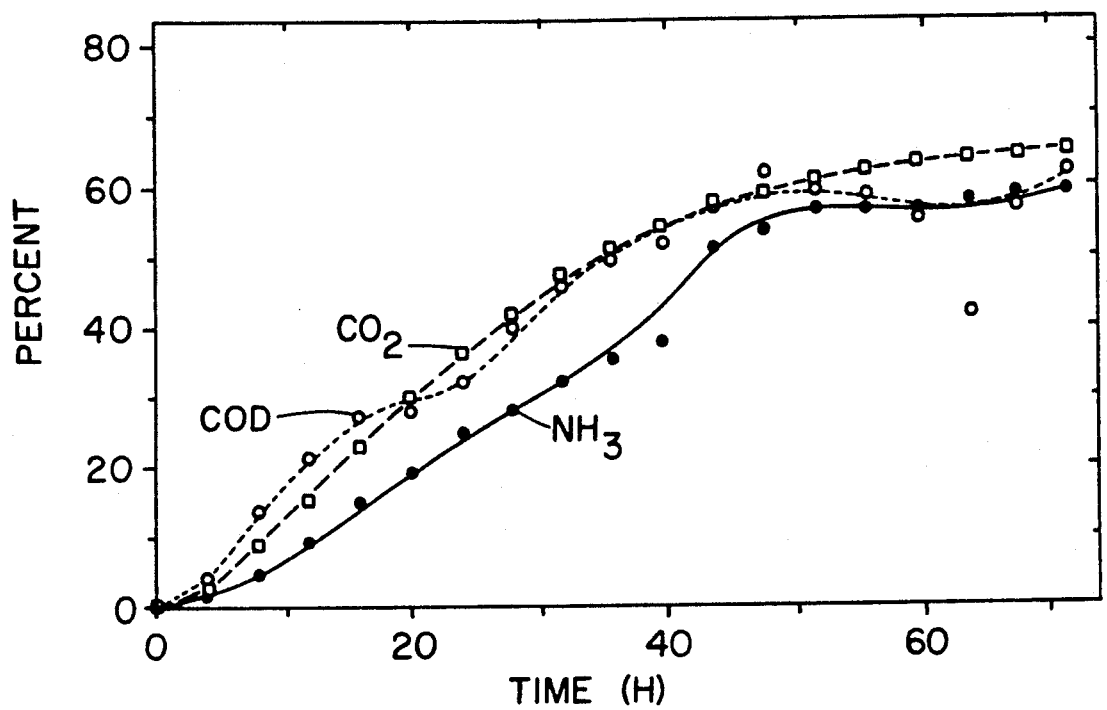
FIG._3A.
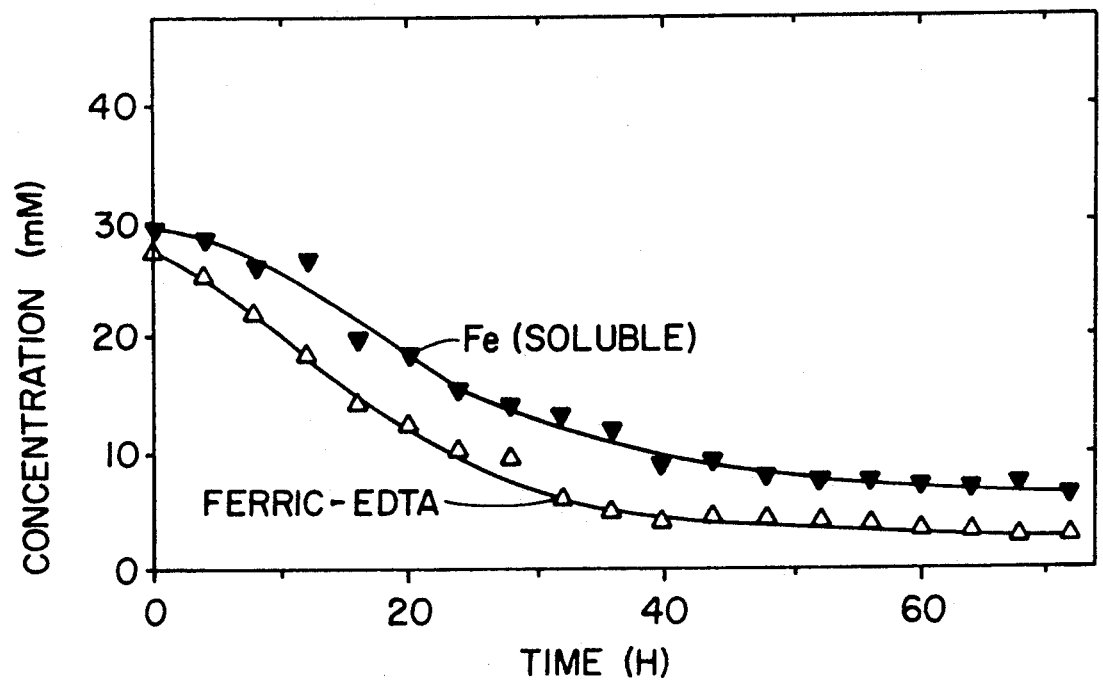
FIG._3B.

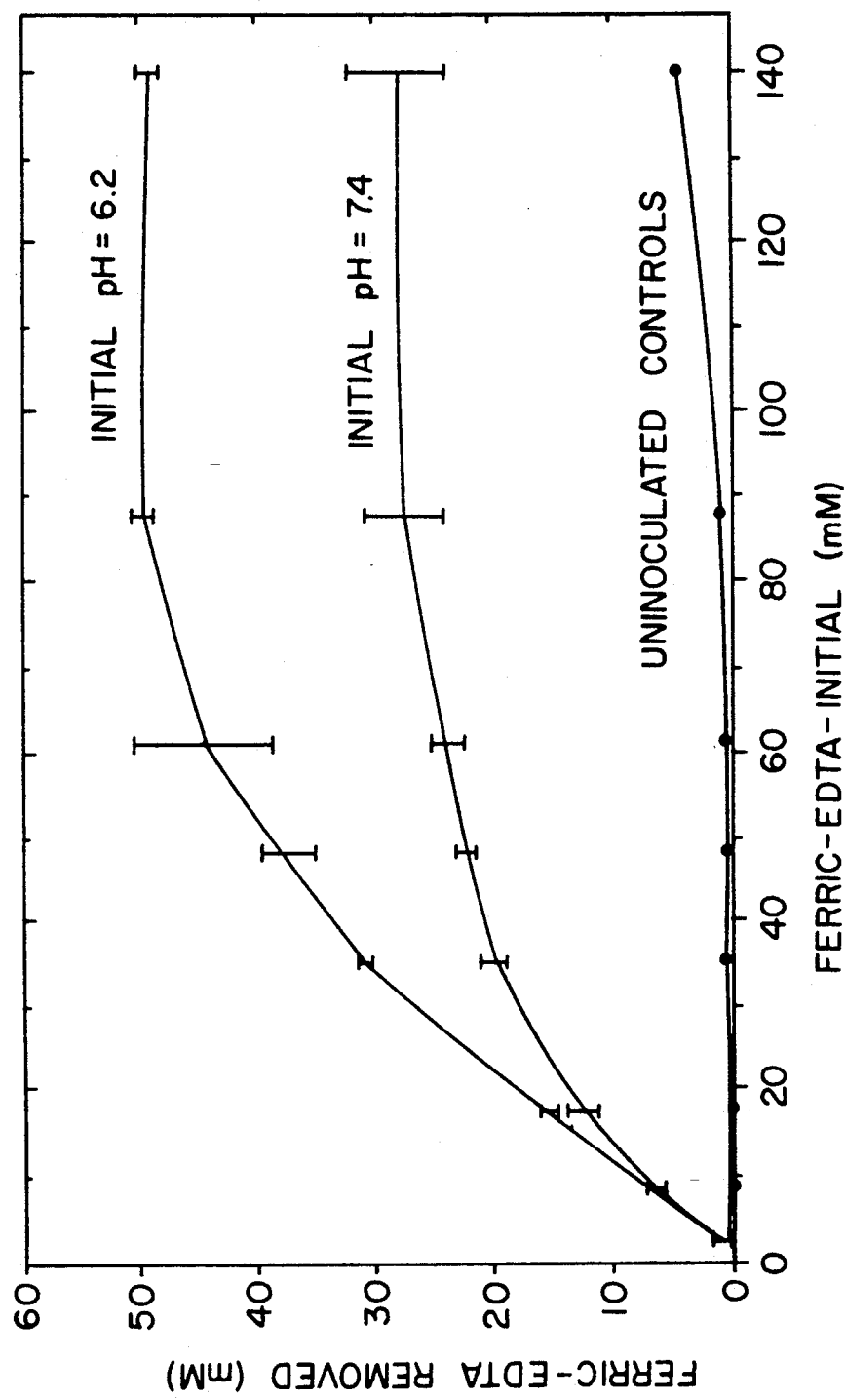
FIG._4.

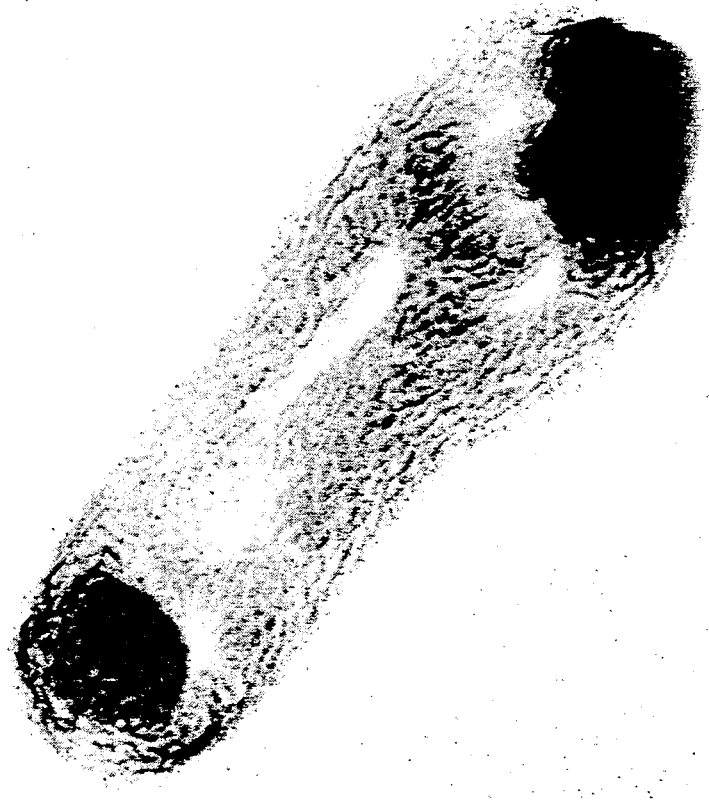
FIG._5

FIG._6

DEGRADATION OF FERRIC CHELATES BY A PURE CULTURE OF AGROBACTERIUM SP.

This is a continuation-in-part of application Ser. No. 07/507,931, filed Apr. 11, 1990, now abandoned.

BACKGROUND OF THE INVENTION

1. Field of the Invention

The present invention relates to biological degradation of ferric chelates of aminopolycarboxylic acids. More particularly, the invention relates to the use of the microorganism *Agrobacterium sp.* to degrade these compounds, especially from aqueous solutions, as well as to biologically pure cultures of *Agrobacterium sp.*

2. State of the Art

It has heretofore been recognized that metal chelates of aminopolycarboxylic acids, such as ferricethylenediaminetetraacetic acid (ferric-EDTA) and other similar chelates, were not readily biodegraded. See, for example. Gerike et al., *Ecotoxicology and Env. Safety*, 3:159-173 (1975).

This inability to readily degrade such metal chelates leads to numerous environmental concerns. In particular, in secondary treatment with an activated sludge, the biodegradation of these metal chelates is so slow that these chelates have been reported to pass through secondary treatment facilities and discharged into the environment without notable degradation. See Thom et al., *Proc. Roy. Soc. of London*, 189:347-357 (1975). This has led to concerns for the possible bioaccumulation of the chelate in the environment as well as the possible transport of heavy metals by release of high concentrations into polluted rivers or sediments. Additionally, EDTA has also been implicated in the mobilization of radionuclides from nuclear waste disposal sites.

On the other hand, accumulation of EDTA in the environment over time periods on the order of years has been shown to be unlikely. For example, EDTA contamination in soil, at relatively low concentrations (2-1000 micrograms per gram of soil), have been demonstrated to be biologically removed. See Tiedje, *Appl. Microbiol.*, 30:327-329 (1975) and Tiedje. *J. Environ Qual.* 6:21-26 (1977). In these studies, the disappearance of low concentrations of EDTA and its metal chelates was shown to occur in 15-45 weeks on a wide variety of soils. However, no single bacterial type was isolated which was capable of metabolizing EDTA or its metal chelates.

At somewhat higher concentrations (<2 mM) in aqueous solution, Belly et al., *Appl. Microbiol*, 29:787-794 (1975) have investigated the aerobic bacterial degradation of the $Fe^{+3}$ EDTA chelate by an acclimated mixed population of bacteria. Disappearance of more than 90% of the substrate in 5 days was observed at these concentrations. Again, no single bacterial type was isolated which would grow on the ferric-EDTA substrate as sole carbon source.

The abstract for SU 525627 describes removal of heavy metal complexes from water by precipitation, using first a sodium hydroxide treatment and then biological purification using aerobic microorganisms. The filtrate obtained from the sodium hydroxide treatment is purified with microorganisms at a pH of 8-9.

Japanese Laid-Open Patent Application (Kokai) No. 58-43782 states that strains of the genera Pseudomonas and Alcaligenes are capable of degrading EDTA under aerobic conditions. The maximum concentration tested was 5 mM and required 5 days for 80% degradation.

Besides biological degradation, the ferric chelate of EDTA can be degraded by ultraviolet irradiation. Specifically, under simulated environmental conditions, Lockhart et al., *Env. Sci. and Technol.*, 9:1035-1038 (1975) as well as Lockhart et al., *Environ. Lett.*, 9:19-31 (1975) have demonstrated degradation by the mechanism of UV irradiation. Rates of degradation in bright sunlight were found to vary from 1-2 days for removal of the parent compound at an initial concentration and pH of 1.6 mM and 4.9, respectively, to greater than 10 days at an initial concentration and pH of 9.8 mM and 6.9, respectively. In these studies transformation of ferric-EDTA was demonstrated but extensive mineralization was not.

In view of the above, there is a continuing need in the art for an efficient method for the degradation of metal chelates of aminopolycarboxylic acids, especially from industrial waste solutions contaminated with such chelates. There is a further need in the art that any such degradation process for the removal of such chelates be conducted rapidly without damaging the environment.

SUMMARY OF THE INVENTION

The present invention is directed to the discovery that the microorganism *Agrobacterium sp.* (deposited with the American Type Culture Collection, Rockville, Md., as ATCC No. 55002) rapidly and efficiently degrades ferric chelates of aminopolycarboxylic acids and accordingly, this organism can be used to treat aqueous solutions so as to remove such ferric chelates.

Accordingly, in one of its composition aspects, the present invention is directed to a biologically pure culture of the microorganism *Agrobacterium sp.*, ATCC number 55002.

In another of its composition aspects, the present invention is directed to a biologically pure culture of *Agrobacterium sp.*, which culture is capable of degrading ferric chelates of aminopolycarboxylic acids from an aqueous solution containing one of more of the chelates.

In one of its method aspects, the present invention is directed to a method of degrading ferric chelates of aminopolycarboxylic acids which comprises combining said chelates with a biologically pure culture of *Agrobacterium sp.* This aspect of the invention further relates to a method for degrading ferric chelates of ethylenediaminetetraacetic acid, propylenediaminetetraacetic acid or mixtures thereof which comprises combining one or more of said chelates with a biologically pure culture of *Agrobacterium sp.*

In another method aspect, the present invention is directed to a method of recovering iron from an aqueous solution containing ferric chelates of aminopolycarboxylic acid which method comprises a) adding a biologically pure culture of *Agrobacterium sp.* to an aqueous solution containing one or more ferric chelates of aminopolycarboxylic acid;

b) maintaining the aqueous solution at a pH of about 8 or less at a temperature and for a period of time sufficient for iron to precipitate from solution; and c) recovering said iron.

BRIEF DESCRIPTION OF THE DRAWINGS

FIGS. 1(*a*) and 1(*b*) illustrate characteristics of the growth of *Agrobacterium sp.* (ATCC No. 55002) in shakeflasks with sodium ferric-EDTA. Solutions containing basal medium (described below), 35 mM sodium ferric-EDTA and 100 mM phosphate were adjusted to pH 6.2 and 7.4 by the addition of HCl and NaOH respectively. The incubations proceeded in shaker-incubators at 29° C. In FIG. 1(a), the optical densities at 600 nm are plotted for aliquots diluted in 0.1 N HCl with the plotted values corrected for the dilution factor. In FIG. 1(b), ferric-EDTA concentration is plotted in millimolar units and the measured pH is given above the data points.

FIGS. 2(a) and 2(b) illustrate results obtained from incubation of *Agrobacterium sp.* (ATCC No. 55002) at the 1 liter scale with pH controlled at 7.4 and temperature maintained between 29°–31° C. The initial broth was prepared to contain 35 mM sodium ferric-EDTA and 100 mM phosphate in basal medium. In particular, FIG. 2(a) illustrates Chemical Oxygen Demand (COD) measurements at different times during the incubation. Specifically, aliquots of the whole broth were taken for COD measurements (COD with cells) and after centrifugation at 13000 g to remove cell mass and any chemical precipitate (COD supernatant). FIG. 2(b) illustrates the concentration of soluble iron (i.e., in solution), of ammonia and of ferric-EDTA at different points of the incubation.

FIGS. 3(a) and 3(b) illustrate results (including carbon and nitrogen mass balance) from a large scale (7.2 liter) incubation of *Agrobacterium sp.* (ATCC 55002) with ferric-EDTA. The COD values were obtained for aliquots after centrifugation to remove cells. The conversion of carbon and nitrogen from ferric-EDTA to $CO_2$ and ammonia are plotted as percentages of the maximum values possible from the initial concentration of ferric-EDTA measured at the time of inoculation. The percentage of COD removed is calculated by subtracting that remaining in solution from that in the initial broth. Neither COD nor ammonia values were corrected for evaporation.

FIG. 4 illustrates the effect of initial pH and ferric-EDTA concentration on the growth of *Agrobacterium sp.* (ATCC 55002). Test tubes contained basal medium, phosphate buffer (100 mM) and sodium ferric-EDTA at the concentrations indicated in the Figure. Test tubes were inoculated at a calculated initial Optical Density (OD) of 1.0 from a concentrate of freshly harvested and washed cells and were incubated at 30° C.±1° C. for 48 hours. Error bars indicate the standard deviation for triplicate experiments (pH 7.4) and duplicate experiments (pH 6.2). Controls were not run in replicate.

FIG. 5 is an electron micrograph of *Agrobacterium sp.*, platinum/palladium shadowed, grown on tryptic soy broth agar plates.

FIG. 6 is an electron micrograph of *Agrobacterium sp.*, platinum/palladium shadowed, grown on ferric-EDTA agar plates. The small dark patches indicate localized high-density regions on the surface of the bacterium.

DETAILED DESCRIPTION OF THE PREFERRED EMBODIMENTS

A biologically pure culture of *Agrobacterium sp.*, ATCC No. 55002, was isolated from a treatment facility receiving industrial waste containing the ferric chelate of ethylenediaminetetraacetic acid (ferric-EDTA) and is capable of degrading ferric chelates of aminopolycarboxylic acids at rates and substrate concentrations significantly greater than any previously reported. This microorganism is an aerobic, gram negative rod of approximately 1 micron in diameter and approximately 2–3 microns in length. For purposes of this application, a biologically pure culture of *Agrobacterium sp.* is a culture which contains cells of one kind, all progeny of a single ancestor or identical ancestors as well as mutants and variants thereof having the distinguishing features of *Agrobacterium sp.*

It has been discovered that the isolated *Agrobacterium sp.* microorganism metabolizes ferric-EDTA as the sole carbon source with a rate of consumption as rapid as 24 mM/day. Preferably, in aqueous solutions, the ferric-EDTA concentrations can range from about 1 mM or less up to about 150 mM or more and more preferably from about 3 mM up to about 80 mM. Thus, the microorganism of the invention is capable of degrading ferric-EDTA at a rapid rate and at high substrate concentrations. As metabolism proceeds, carbon dioxide and ammonia are produced, pH rises, and iron is precipitated. The precipitated iron can be recovered by any conventional means such as filtration, centrifugation, etc. The isolated microorganism, *Agrobacterium sp.*, also metabolizes the ferric chelates of other aminopolycarboxylic acids, such as propylene diaminetetraacetic acid (PDTA) and the like.

For purposes of this application, the term "ferric chelates of aminopolycarboxylic acid" means those aminopolycarboxylic acids having two or more amino group and 3 or more carboxylic acid groups and which are capable of forming chelates with $Fe^{+3}$. Aminopolycarboxylic acids which may be degraded (as the ferric chelate) by the microorganism of the invention include, for example, ethylenediaminetetraacetic acid (EDTA), propylenediaminetetraacetic acid (PDTA), and the like.

A biologically pure culture of the newly discovered microorganism, *Agrobacterium sp.*, can be used in a process for the removal of ferric chelates of aminopolycarboxylic acids. Preferably, the process is conducted in an aqueous solution wherein the aqueous solution is maintained at a pH of about 8.0 or less. Alternatively, it is contemplated that the process can be conducted in a landfill, or other similar site, which has been contaminated with ferric chelates of aminopolycarboxylic acids. As before, it is preferable for the pH of the medium to adjusted to a pH of about 8.0 or less.

When conducted in an aqueous solution, it is contemplated that the process is useful with a wide variety of aqueous solutions such as industrial waste solutions, cleaning solutions, among others. Additionally, the aqueous solution employed herein should not contain biocidal effective amounts of a biocide. In a preferred embodiment, in order to enhance the degradation rate of ferric chelates, the aqueous solution should contain less than an inhibitory effective amounts of inhibitors of *Agrobacterium sp.*, i.e., an amount of an inhibitory agent which causes a 50% decrease in ferric-aminopolycarboxylic acid metabolism.

In preferred embodiments of the process of the invention a mineral and biotin stock is added to the aqueous solution. Specifically, the salts ammonium chloride, magnesium sulfate and calcium sulfate can be used at concentrations of 5 mM, 0.1 mM and 0.07 mM respectively. In these embodiments, certain trace mineral salts are added to the aqueous solution from which the ferric chelates are to be degraded in order to provide an improved media for growth of the microorganisms. These salts may include $H_3BO_3$, $MnSO_4.7H_2O$, $ZnSO_4.7H_2O$, $CuSO_4.H_2O$, $(NH_4)_6Mo_7O_{24}.H_2O$, $CoSO_4.7H_2O$. The trace salts preferably are present in amounts of less than about 25 micromolar. Specifically, these salts can be employed at concentrations of 0.025 mM, 0.003 mM, 0.002 mM, 0.00035 mM, 0.0002 mM and 0.00004 mM respectively. Biotin may also be added to the solution and typically is present in amounts of about 1 to about 10 micromolar. Specifically, biotin can be employed at a concentration of 2 micromolar. Aqueous solutions containing the specific concentrations recited above of the salts, trace mineral salts, and biotin are sometimes referred to herein as "basal medium".

Other ingredients which may be present in the aqueous solution include compatible buffers, i.e., buffers which are not toxic to the microorganism, such as sodium phosphate, potassium phosphate, and the like. A sufficient amount of buffer is added so as to maintain the pH of the aqueous solution in the desired range. The preferred buffer for the process of the invention is phosphate buffer, e.g., a 50/50 molar mix of sodium and potassium salts at a total phosphate concentration of from 25 to 200 mM. However, any compatible buffer or buffers can be used if acid is periodically added to maintain the pH at a level of below about 8.0. Preferably, the pH of the aqueous solution is maintained between about 6 and 8 and preferably, the buffer or buffers are added to the aqueous solution generally are present in amounts of about 25 mM to about 200 mM.

In order to maintain the aqueous solution at a pH of about 8.0 or less, acid may be added to the solution. The acid can be any acid which does not affect the degradation of the ferric chelates by the *Agrobacterium sp.* microorganism. Such acids include, HCl, $H_2SO_4$, and the like. Preferably, HCl is used. The acid is added periodically to keep the pH below about 8.0.

The temperature of the aqueous solution containing both the metal chelate and *Agrobacterium sp.* is not critical provided that a temperature is employed which is compatible with the microorganism. Accordingly, any temperature may be employed which is sufficient to allow the microorganism to degrade ferric chelates. In preferred embodiment, the temperatures employed range from about 21° C. to about 37° C. and even more preferably, from about 29° C. to about 31° C.

The following examples illustrate the isolation, identification and testing of *Agrobacterium sp.* and are provided to further illustrate the invention, but are not meant to limit the scope of the claims in any way.

EXAMPLES

The procedures described below were used to evaluate the microorganism of the invention.

Bacterial isolations. Samples of sludge were obtained from an aerated secondary waste treatment facility that had been receiving wastes containing ferric-EDTA for several years. Samples were collected in plastic bottles, transported on ice and then held at 4° C. prior to use. An enrichment medium (EDTA EM, See Table 1) was inoculated with 100 microliter of sample and incubated at 30° C. for two weeks. Growth from this initial enrichment was streaked onto agar plate medium (agar solidified EDTA EM) and incubated at 30° C. until growth was observed. Bacterial colonies from these plates were repeatedly transferred and tested for growth on a stringent agar medium (EDTA M1 and M2, see Table 1) to select for colonies using ferric-EDTA as sole carbon source. Isolated colonies on these media were then transferred to aerobic liquid culture media containing ferric-EDTA as sole carbon source (EDTA G1, see Table 1).

TABLE 1

Enrichment, Isolation and Growth Media[a]

| Ingredient | Concentration (mM) in Media | | | |
|---|---|---|---|---|
| | EDTA EM | EDTA M1 | EDTA M2 | EDTA G1 |
| Citrate-phosphate buffer | 50 (pH 5.5) | | | |
| MES[b] | | 50 (pH 6) | | |
| Phosphate buffer | | | 50 (pH 6) | 100 (pH 7.4) |
| $Na_2S_2O_3 \cdot 5H_2O$ | 40 | 40 | 40 | |
| Ferric-EDTA | 5[c] | 5[c] | 5[c] | 35[d] |
| $NaHCO_3$ | 24 | | | |
| Agar | 17 g/L[e] | 17 g/L | 17 g/L | |

[a]All media employed the mineral and biotin base described at page 10 hereinabove as the basal medium.
[b][N-Morpholino]ethanesulfonic Acid
[c]Ammonium salt.
[d]Sodium salt.
[e]No agar in liquid enrichment medium EDTA EM In all studies, media containing ferric-EDTA were sterilized prior to incubation with *Agrobacterium sp.* In some cases, this was done by filtration through 0.2 micron filters after addition of all components and after adjustment of pH. In other cases, the total broth was not filtered, rather stock solutions were filter sterilized individually and then added together at which time the pH was adjusted using an ethanol-washed pH electrode to maintain sterility. In still other cases, the stock solutions, with the exception of biotin, were heat sterilized in situ. Then a stock solution of $FeCl_3$ (0.1 M) was prepared for supplementation of iron at 1 mM. The biotin and $FeCl_3$ stocks were filter sterilized and added separately. Media which was inadvertently contaminated with organism(s) other than *Agrobacterium sp.* did not support extensive degradation of ferric-EDTA and, accordingly, media containing such other organism(s) are not preferred.

Cell Harvest and Storage. After growth in ferric-EDTA media, cells were harvested by centrifugation at 4° C. Broth was first centrifuged at 4200 g for 20 minutes and then the supernatant fluid was decanted and centrifuged at 13000 g for 20 minutes. The cell pellet was resuspended in sterile distilled water and centrifuged again at 13000 g to wash the cells. The precipitated cell pellet was resuspended in sterile distilled water at an optical density >5 at 600 nm. For long term storage, glycerol was added (10% by volume) to the suspension and aliquots (2 ml) stored in a liquid nitrogen freezer.

The procedure given above for washing the inoculum before storage or inoculation of fresh media was adopted to produce conditions which would lead to rapid degradation. In several instances when unwashed inocula were used, growth in fresh media either lagged or was considerably slower than that normally observed. Washing removes much of the precipitate as determined by light microscopy.

Alternatively, the cells can be grown in a complex trypticase/soy broth (from BBL) maintained at 29°–31° C. for 24 hours. The cells so grown are still effective in degrading ferric-EDTA when added to an aqueous solution containing ferric-EDTA.

For inoculation, cells from frozen stocks were added or cells were harvested from seed flasks in the later stages of growth. When freshly harvested, cells were prepared as above except that after the initial centrifugation at 13000 g, the cells were suspended in water or fresh media as the inoculation medium.

Electron Microscopy. Cultures were fixed with 2% glutaraldehyde in 0.1 M cacodylate buffer for 2 minutes and then dropped onto Formvar coated grids, dried and vacuum coated with platinum/palladium at an angle of 14 degrees. Photomicrographs were obtained with rotary shadowing on a JEOL—100 CX electron microscope.

Strain Identification. Representative samples were subcultured on blood agar and McConkey agar plates. After incubation, samples were prepared for identification by Vitek AMS using the GNI Card (Vitek Systems, Inc., Hazelwood, Mo. 63042) and API 20E using the API Rapid NFT (API Analytab Products, Plainview, N.Y. 11803) systems for the identification of bacteria by the analysis of biochemical reactions. In addition, gas chromatographic analysis of whole cell fatty acids as described in Drucker, *Methods in Microbiology*, Vol. 9, J. R. Norris, Ed. Academic Press, London, p. 51–125, was also used to confirm the identification.

Ferric-EDTA Assay. Cells were separated from samples prior to the determination of ferric-EDTA by centrifugation in an Eppendorf Model 5415 centrifuge at 14,000 rpm for 2 minutes. Samples were then diluted with water or initial mobile phase such that the maximum ferric-EDTA concentration of the diluted samples was less than 0.9 mM.

HPLC analysis were performed using a modular Waters Associates system (Millipore Corp., Milford, Mass. 01757) equipped with a WISP 712 sample processor for injection of samples, two Waters 510 pumps for mobile phase delivery, a Waters 490 multiwavelength detector set at 360 nm for detection of the ferric-chelate and a Waters 840 data system for display, storage, plotting and analysis of the chromatograms.

The chromatographic separations were obtained after injection of 30 microliters of sample onto a commercially available, 15 cm long by 4.6 mm i.d. reversed-phase HPLC column (LC18 from Supelco, Inc., Bellefonte, Pa. 16823). Isocratic elution at 1.0 milliliter/minute with an initial mobile phase consisting of 1 g/liter ammonium acetate, 0.5 g/liter PDTA, 1.5 milliliter/liter glacial acetic acid, 0.5 milliliter/liter ammonium hydroxide, 0.1 milliliter/liter triethylamine and 5 milliliter/liter acetonitrile in deionized water caused elution of ferric-EDTA at 2 minute retention time. After 2.5 minutes from the injection, a step-gradient to a final mobile phase consisting of 0.5 g/liter PDTA, 0.1 milliliter/liter triethylamine and 600 milliliter/liter acetonitrile in deionized water for 5.5 minutes washed highly retained components from the column. A further step gradient to the initial mobile phase for 4 minutes was used to reequilibrate the column.

The instrument was calibrated daily by the injection of a series of standards of ammonium ferric-EDTA in unbuffered, deionized water encompassing the concentrations from 0.03 to 0.9 mM. Linear-least squares regression analysis of the area responses of the standards was used to obtain slope and intercept values (r-squared typically >0.996) which were then used to obtain quantitative values for samples from the measured area. Precision and accuracy were estimated to be better than 5% relative over the calibration range.

Ammonia/Ammonium Assay. Total ammonia was determined using an Orion Model 95-12 ammonia electrode (following the procedures set forth in the Orion Model 95-12 instruction manual, Orion Research Inc.).

COD Assay. For the estimation of COD in samples, the test tube colorimetric procedure of the Hach Chemical Co. (Hach Co., Loveland, Col. 80539), which is similar to Method 508C in "Standard Methods for the Examination of Water and Wastewater" American Public Health Association, Washington, D.C., 16th Edition, pp. 532–538 (1985) was used.

Iron Assay. For the estimation of total iron in aqueous samples, a modification of Stookey's ferrozine procedure described in Stookey, *Anal. Chem.*, 42:779–781 (1970) was used. To release the iron cation from chelators present, including ferric-EDTA, samples were first digested using a procedure adapted from Method 302E in "Standard Methods for the Examination of Water and Wastewater", American Public Health Association, Washington, D.C., 16th ed. p. 148 (1985). A 50-microliter sample was added to an acid-cleaned, thick-walled, screw-capped test tube (equivalent to Hach COD test tubes), followed by 50 microliters of concentrated nitric acid and 100 microliters of concentrated sulfuric acid. The test tube was tightly-capped and heated to reflux at 150° C. for 15 minutes in a Hach Reactor Plate. After cooling, the tubes were uncapped and replaced in the reactor for a maximum of 10 minutes, but not long enough for the test tube to become thoroughly dry. After cooling, 200 microliters of acid-ferrozine reagent (0.514 g ferrozine, 10 g hydroxylamine hydrochloride, and 50 milliliters of concentrated hydrochloric acid dissolved and diluted to 100 ml with distilled water) was added. The contents were mixed using a vortex mixer and then 1.5 milliliters of buffer (40 g ammonium acetate and 35 milliliters of concentrated ammonium hydroxide diluted to 100 milliliters with distilled water) was added to adjust the pH between 5 and 9. The sample was then diluted with 5.4 milliliters of distilled water.

Standards encompassing the concentration range from 20 to 1000 mg/L total iron were prepared from pure ferric ammonium sulfate dodecylhydrate. Standards were treated as the samples were. From the absorbance of the standards measured at 562 nm in a spectrophotometer (Hach DR/3) and concentrations of the standards, a linear least squares calibration was constructed. At concentrations of total iron greater than 50 mg/L, the observed precision and accuracy using samples containing known concentrations of ferric-EDTA were better than 5%.

EXAMPLE 1

Bacterial Identification

The identification of the isolated strain as *Agrobacterium sp.*, a gram-negative aerobe, was made on a Vitek AMS (Vitek Systems, Hazelwood, Mo. 63042-2395) using a Vitek GNI Card (gram negative identification card; product no. 51-1306) with a probability of 99%. The biochemical tests employed for the identification and the results for the isolated strain are presented in Table 2. The identification was also confirmed by an API Rapid NFT strip (API Analytab Products, Plainview, N.Y. 11803; product no. 8886-500951) with a probability of 99.9%. The biochemical tests employed for the identification and the results for the isolated strain are presented in Table 3. Gas-chromatographic analysis of the fatty acid composition of the strain also confirmed the genera as Agrobacterium.

TABLE 2

Vitek GNI Test Results for Isolated Strain

| Biochemical Test: | Reaction | Biochemical Test: | Reaction |
|---|---|---|---|
| Dp-300 | − | Sorbitol | − |
| Glucose | + | Sucrose | − |
| Acetamide | − | Inositol | − |
| Esculin | + | Adonitol | − |
| Plant Indican | + | p-Coumaric | − |
| Urea | + | $H_2S$ | − |
| Citrate | − | ONPG | − |
| Malonate | − | Rhamnose | − |
| Tryptophan | − | Arabinose | + |
| Polymyxin B | − | Glucose (ferment.) | − |
| Lactose | + | Arginine | − |
| Maltose | + | Lysine | − |
| Mannitol | + | Ornithine | − |
| Xylose | + | Oxidase | + |
| Raffinose | − | | |

TABLE 3

API Rapid NFT Test Results for Isolated Strain

| Carbon Source: | Growth | Biochemical Test: | Reaction |
|---|---|---|---|
| D-Glucose | + | Nitrate Reduction | + |
| L-Arabinose | + | Tryptophanase | − |
| D-Mannose | + | Glucose fermentation | − |
| D-Mannitol | + | Arginine dihydrolase | − |
| N-acetyl-D-glucosamine | + | Urea | − |
| Maltose | + | Esculin | + |
| D-Gluconate | + | Gelatinase | − |
| Caprate | − | Beta-galactosidase | + |
| Adipate | − | | |
| Malate | + | | |
| Citrate | − | | |
| Phenylacetate | − | | |
| Oxidase | + | | |

In view of the above results, the microorganisms was tentatively determined to be *Agrobacterium radiobacter*. In addition, the isolate was typed independently (American Type Culture Collection, Rockville, Md.) as an *Agrobacterium sp.* with distinction between biovar 1 and biovar 2 not determined. Accordingly, this microorganism is referred to herein as *Agrobacterium sp.*

EXAMPLE 2

Growth studies

Growth studies were carried out to determine various characteristics of the microorganisms. For these studies, the basal medium recited at page 9 hereinabove was employed as well as 100 mM phosphate buffer, and 35 mM sodium ferric-EDTA in Fernbach flasks. Incubation was at 29° C. in a shaker-incubator. Samples were taken periodically and the pH, ferric-EDTA concentration and optical density (OD) at 600 nm were determined. The pH was measured using an Orion combination electrode and a Corning pH meter. OD was used as a measure of bacterial growth. Measurements were made by dilution in 0.1 N HCl to dissolve the iron precipitate which formed during degradation and which interfered in reading OD due to bacterial growth.

The increase in OD observed during growth in the Fernbach flasks is shown in FIG. 1(a).

In FIG. 1(b), the concentration of ferric-EDTA in the flasks is plotted along with the measured pH. The plots demonstrate that as the optical density increases in all three flasks, the concentration of ferric-EDTA decreases and the pH increases. When pH does not increase, no metabolism of ferric-EDTA is observed in any of the flasks. Conversely, if the pH is not constrained from increasing above pH 8, the disappearance of ferric-EDTA stops. The apparent increase of ferric-EDTA concentration in the flask without pH adjustment is caused by evaporation after ferric-EDTA metabolism has ceased (pH > 8.1). No correction for evaporation from any of these flasks was made. The data contained in these figures demonstrates that *Agrobacterium sp.* grows while ferric-EDTA is being degraded and when degradation ceases, so does growth.

EXAMPLE 3

Incubation at the 1 liter scale

The isolate was grown at the 1 liter scale in a 2 liter incubator to enable the control of pH. The initial incubator broth was 35 mM in sodium ferric-EDTA, 100 mM in phosphate, and contained the basal medium described above. In addition, $FeCl_3$ was added to 1 mM final concentration. For inoculation of the incubator, the strain was grown in a shakeflask at 31° C. in the same media as above for 24 hours. The cells from the shakeflask were separated from the broth by centrifugation for 20 minutes at 13000 g. These were resuspended in 200 mL of fresh broth and added to the incubator to bring the initial total volume to 1 liter.

Air was passed into the Multigen fermentor (New Brunswick Scientific Inc., Edison, N.J. 08818) through a 0.2 micron sterile filter at a flowrate of 1 liter/minutes. The fermentor (incubator) was stirred with a magnetically driven propeller shaft at 500 rpm. The hydrogen ion concentration was monitored and controlled at between pH 7.4 and 7.7 by the automatic addition of HCl. Temperature of the incubator was maintained at 30° C.±1° C.

The results are plotted in FIGS. 2(a) and 2(b). The decrease in ferric-EDTA concentration observed as the incubation proceeded was accompanied by a parallel decrease in iron concentration in solution. As the substrate was being removed from aqueous solution, the ammonium content increased. In addition, COD fell, but not in proportion to the decrease in ferric-EDTA concentration (93%). For samples measured after centrifugation to remove the cell mass and precipitate, COD fell from 8880 to 2640 mg $O_2$/liter (70% decrease); for samples measured with cells and precipitate still present, COD fell from 8870 to 3392 mg $O_2$/liter (62% decrease).

In addition, selected samples were diluted and plated on TSA for bacterial counting. The live bacterial count began decreasing between 46 and 70 hours after the beginning of the experiment. This coincides closely with breaks in the slopes of the curves.

EXAMPLE 4

Inhibition

The inhibitory effect of several factors on ferric-EDTA metabolism was investigated. These experiments were carried out in test tubes using a standard set of conditions: 100 mM phosphate buffer (pH 7.4); basal medium described above; 35 mM in ferric-EDTA; inoculation to an optical density of 1 at 600 nm; initial volume of 3.5 mL; incubation at 29°–31° C. for 1 to 4 days in a test tube shaker incubator. Concentrates of the factors to be tested for inhibition were added at 4 to 6 different levels to different sterile test tubes with the rest of the volume provided by the addition of deionized water.

The data on the inhibitory effects of several components are summarized in Table 4. The concentrations in the table are those which caused a 50% decrease in metabolism of ferric-EDTA over the time of the experiments compared to controls containing none of the factor tested.

TABLE 4

Inhibition of Strain ATCC #55002
Conc. (mM)
Causing 50% inhibition

| Factor | Ferric-EDTA Metabolism Inhibition |
|---|---|
| Ferric-EDTA | 80 |
| Hepes | <5 |
| Mops | <5 |
| Triethanolamine | 15 |
| Tris | 5 |
| Ionic Strength (NaCl) | 540 |
| Ammonium | 130 |

Hepes - 4-(2-hydroxyethyl)-1-piperazineethanesulfonic acid
Mops - 3-(4-Morpholino)propanesulfonic acid
Tris - tris(hydroxymethyl)aminomethane In addition to inhibition by the specific chemicals listed above, unidentified metabolite(s) of ferric-EDTA degradation by *Agrobacterium sp.* are produced during degradation and lead to product inhibition. Also, this microorganism is inhibited by one or more components found in photoprocessing solutions.

EXAMPLE 5

Chelators as growth substrates

A number of metal chelators were tested as substrates for growth. These experiments were carried out in test tubes which were placed in a benchtop shaker for 24 days at 30° C. The medium was the same as that described above for growth inhibitors except that the initial phosphate buffer concentration was 71 mM and the inoculum was calculated to produce an initial optical density of 0.4. Concentrates of the organic chelators were added to the replicate test tubes at final concentrations of 4 and 20 mM. For samples containing metals, a molar amount equivalent to that of the chelator was added from concentrates of $FeCl_3$, $NiCl_2$ or $CuSO_4$. After addition of all components except the inoculum, the samples were adjusted to pH 7.4 with either dilute HCl or KOH. A duplicate set of test tubes was prepared as above, but with the addition to all samples of 0.25 mL of a 2.5 g/L solution of $HgCl_2$ to prevent bacterial growth.

Growth in the samples after 24 days was assessed by comparing the optical densities of sample tubes with those in the controls with mercuric chloride added (Table 5). Those substrates which had an optical density five-fold greater than the respective controls at both concentrations tested were considered positive for growth.

TABLE 5

| Growth Substrates for Agrobacterium sp. | | | |
|---|---|---|---|
| Substrate | Growth | Substrate | Growth |
| EDTA | — | $Fe^{3+}$EDDA | — |
| $Fe^{3+}$EDTA | + | Ethylene diamine (ED) | — |
| $Ni^{2+}$EDTA | — | $Fe^{3+}$ED | — |
| $Cu^{2+}$EDTA | — | TEA (triethanolamine) | — |
| NTA | — | $Fe^{3+}$TEA | — |
| $Fe^{3+}$NTA | — | Citrate | — |
| $Ni^{2+}$NTA | — | $Fe^{3+}$Citrate | — |
| $Cu^{2+}$NTA | — | Propionate | — |
| PDTA | — | $Fe^{3+}$Propionate | — |
| $Fe^{3+}$PDTA | + | Acetate | — |

TABLE 5-continued

| Growth Substrates for Agrobacterium sp. | | | |
|---|---|---|---|
| Substrate | Growth | Substrate | Growth |
| $Ni^{2+}$PDTA | — | $Fe^{3+}$Acetate | — |
| $Cu^{2+}$PDTA | — | Lysine | — |
| IMDA | — | $Fe^{3+}$Lysine | — |
| $Fe^{3+}$IMDA | — | EDDA | — |

IMDA = iminodiacetic acid
NTA = nitrilotriacetic acid
EDDA = ethylenediamine diacetic acid

EXAMPLE 6

Incubations at the 7.2 liter scale

In order to control aeration, mixing and pH better and to determine the carbon and nitrogen mass balance, incubations were run at volumes of 7.2 liters in computer controlled 14 liter Chemap CF 3000 incubators (Chemap AG, Volketswil, Switzerland) maintained at 28° C.

Two 6 liter batches of ferric-EDTA medium containing basal medium (described above) were inoculated with freshly harvested cells concentrated in 1.2 liters of the same basal medium. One of the incubations also received a steady feed of 250 g/L sucrose and 250 g/L yeast extract at a constant rate of 0.2 g/min. This feed composition was chosen based on previous work with the cultivation of Agrobacteria in Hofer, *J. Bacteriology*, 41:193-224 and Lippincott et al, *The Prokaryotes*, Vol. 1, Starr et al, Eds. Springer-Verlag, pp. 842-845.

FIG. 3(a) is a graphical representation of the cumulative conversion of ferric-EDTA to $CO_2$ and to $NH_3$ as percentages of the maximum possible from ferric-EDTA in the incubation with only ferric-EDTA as the carbon source. In addition, the percentage decrease in COD is also plotted. All three curves parallel each other and further demonstrate that ferric-EDTA is efficiently mineralized. FIG. 3(b) plots the relative concentrations of soluble iron and ferric-EDTA during the course of the incubation supplied solely with ferric-EDTA as carbon source.

In the incubation with additional carbon and/or nitrogen sources (sucrose/yeast), degradation of ferric-EDTA and growth of the microorganism was less vigorous, although substantial degradation did occur. In particular, for the same duration of incubation, 37% of the ferric-EDTA was degraded as opposed to more than 85% for the case shown in FIG. 3(b). Accordingly, substantial degradation of ferric-EDTA in waste streams containing non-biocidal carbon sources can be expected.

EXAMPLE 7

Effect of ferric-EDTA concentrations on Degradation by *Agrobacterium sp.* (ATTC 55002)

To determine the maximum initial ferric-EDTA concentration that the isolate would tolerate, a series of test tube incubations using the basal medium (described above) buffered with phosphate at 100 mM were carried out for 48 hours at 30° C.±1° C. The initial ferric-EDTA concentration was varied from 2.9 to 140 mM. The values for the concentration removed (calculated by subtracting the concentration remaining at 48 hours from the concentration initially added) are plotted in FIG. 4. No pH adjustments were made during this experiment.

The extent of degradation was related to the initial pH. At the lower initial pH, for all concentrations tested more ferric-EDTA was degraded. The degradation proceeded to consume 48 mM of substrate at an initial pH of 6.2 and 28 mM at pH 7.4. In both sets of data, the maximum degradation extended to the highest concentrations tested.

At the higher initial hydrogen ion concentration (pH 6.2), ferric-EDTA is metabolized at a limiting rate of 24 mM/day while at the lower initial hydrogen ion concentration (pH 7.4), the maximum rate is 15 mM/day.

EXAMPLE 8

Morphology

Cells of the isolate were grown on agar plates containing either tryptic soy broth or ferric-EDTA as sole carbon source (see Table 1, medium G1 with 17 g/L agar). Electron micrographs of several aliquots of each culture were taken as described above. Examples of these are reproduced in FIG. 5 (tryptic soy broth) and FIG. 6 ferric-EDTA. In both cases the culture consisted of rods from approximately 2-3 microns long by approximately 1 microns in diameter. Only on microbes grown on ferric-EDTA were small dark patches noted.

As described in the Examples, a culture of *Agrobacterium sp.* can be used in a process for the degradation of ferric chelates of aminopolycarboxylic acids. The process preferably employed on aqueous solutions containing such ferric chelates and is particularly suitable for degrading ferric-EDTA, ferric-PDTA, or mixtures thereof from aqueous solutions. The rate and extent of degradation are dependent on the pH, or hydrogen ion concentration. As biodegradation proceeds and such ferric chelates are consumed, both cell mass and pH increase. If the hydrogen ion concentration is allowed to fall much below $10^{-8}$ (pH greater than about 8), degradation and growth cease. By the addition of acid periodically to constrain pH from rising above about 8, more extensive degradation occurs.

Without being limited to any theory, in these experiments it is believed that the source of at least some of the increase in pH can be accounted for by the production of ammonia which is observed to increase in concentration as the ferric-EDTA is metabolized. Although ammonia itself inhibits growth of the microorganism (Table 4), significant inhibition, i.e., 50% or more, appears at a higher concentration than the concentration produced in these incubations.

The degradation of the aminopolycarboxylic acids by the *Agrobacterium sp.* is primarily biological, as shown by the Examples. In uninoculated controls, as in those summarized in FIG. 4, neither optical density nor pH significantly increased as the incubation proceeded, nor was a significant decrease of ferric-EDTA concentration observed. Conversely, in inoculated samples, as degradation proceeded, the decrease in ferric-EDTA concentration during incubation was always accompanied by an increase in optical density and pH. Finally, the rapid increase in ammonia/ammonium concentration and the substantial release of $CO_2$ observed in the inoculated samples demonstrates a relatively complete metabolism of the substrate. It is believed that any influence of light on the degradation was minimal or nonexistent.

The efficiency of the mineralization of organic carbon from ferric-EDTA degraded by the microorganism of the invention can be calculated from the data plotted in FIG. 3(a). At 3 days, 64% of the initial carbon can be accounted for by the evolved $CO_2$. The COD remaining in solution at this time, after centrifugation to remove cell mass and associated precipitate, corresponds to 39% (an overestimate since the measured values for COD were not corrected for evaporation) of that initially present. Even accounting for the maximum potential errors associated with both measurements (<10% relative) and the effects of evaporation, less than 20% of the carbon initially present could have been converted to cells.

The data for the 1 liter incubations confirms the relatively small amount of cell mass produced from the biodegradation. At the end of the experiment when the ferric-EDTA concentration remaining in solution was 7% of that initially present, the difference between the COD remaining in the total broth (including cells, precipitate, and soluble metabolites) and that remaining in the solution after the cells and precipitate were removed by filtration (soluble metabolites) was less than 10% of that in the initial fresh broth (752 vs 8870 mg $O_2$/liter). The difference reflects the maximum oxidizable carbon which could have been incorporated into cell mass. Thus, the metabolism of ferric-EDTA by this microorganism leads primarily to mineralization and not to increased cell mass.

In addition to the $CO_2$ and cell mass, an unidentified degradation product or products accumulates in solution. This product(s) is evident from the residual COD present in the solution at the end of the incubation after removal of cells and precipitates. The *Agrobacterium sp.* (ATCC 55002) leads to degradation of 90% or more of the initial ferric-EDTA present. However, the COD reduction only approaches 70%. Thus 20-30% of the carbon initially present as ferric-EDTA remains in solution as unidentified metabolites at the end of the incubation. These metabolites can be inhibitory to the growth of the microorganism.

Although not wishing to be bound by any theory, it is believed that the microorganism of the invention has a requirement for iron. This was indicated by some preliminary growth studies. In some of these a variable and often long lag time (3 days) was observed when attempting to cultivate the strain in ferric-EDTA media which contained a large excess of EDTA. In the normal procedure for preparing media as described above, ferric-EDTA was dissolved in a solution consisting of basal medium and phosphate buffer. After all components were dissolved, the pH of the media was adjusted. As the pH was increased, a red-orange flocculent precipitate characteristic of iron hydroxides formed. The media were then filter sterilized which removes the precipitated iron and leaves an excess of EDTA in solution. The excess becomes greater if the pH is increased further. In fact, in order to ensure minimal lag phase in the larger scale incubations 1 millimolar ferric chloride was added to the sterile-filtered incubator media to replace some of the iron removed by the filtration. This procedure consistently produced minimal lag times of less than a few hours.

Besides a deficit of iron, lag times were also found to be related to treatment of the inoculum. When an inoculum was harvested from spent ferric-EDTA media by centrifugation without washing of the cells, it was observed that, in addition to the cells, a considerable amount of chemical precipitate was present. It is believed that the precipitate is an insoluble iron salt which forms after the strong chelator, EDTA, has been degraded. In some experiments, if most of the precipitate was not removed from the inoculum by washing as noted above, slow growth was observed in subsequent incubations.

The marked preference of this microorganism for ferric-aminopolycarboxylic acids and its effectiveness at relatively high substrate concentrations makes it useful for waste remediation strategies. In uses as a cleaning, decontamination or descaling agent, a large proportion of the EDTA or other aminopolycarboxylic acid used is believed to become chelated with a heavy metal, in many cases iron. If sufficient excess iron is present in, or added to, an aqueous system to force the equilibrium of the non-iron metal chelates to the ferric chelate, the microorganism of the invention can be used in that environment.

Accordingly, another aspect of the present invention relates to a method for the removal of metal chelates of aminopolycarboxylic acid from an aqueous solution containing such chelates wherein the metal is any metal cation, other than $Fe^{+3}$, capable of chelating with said aminopolycarboxylic acid which method comprises:

a) adding a sufficient amount of a ferric salt to the aqueous solution containing said metal chelates so that a substantial portion of said metal chelates become ferric chelates; and b) adding *Agrobacterium sp.* (ATCC 55002) to said solution while maintaining the pH of said solution at about 8 or less.

In general, sufficient amount of a ferric salt is added so that at least about 50% of the metal chelate and preferably, at least about 80% and more preferably at least about 95% is converted to ferric chelates. Suitable ferric salts for use herein include any ferric salt which is soluble in said aqueous solution including without limitation, ferric ammonium sulfate, ferric nitrate, ferric chloride, ferric sulfate, and the like. Further, in this regard, it is noted that certain ferric salts which are insoluble in water but soluble in aqueous acidic solutions may be employed herein by merely employing an acidic aqueous medium in which such ferric salts are soluble and which the microorganism *Agrobacterium sp.* will tolerate.

From the foregoing description, various modifications and changes in the process will occur to those skilled in the art. All such modifications coming within the scope of the appended claims are intended to be included therein.

What is claimed is:

1. A method of degrading ferric chelates of aminopolycarboxylic acids having two or more amino groups and three or more carboxylic acid groups which comprises contacting a biologically pure culture of *Agrobacterium sp.*, ATCC number 55002, with an aqueous solution containing one or more ferric chelates of aminopolycarboxylic acids under conditions suitable for growth of said culture on said chelates, and maintaining the contact between said chelates and the culture until said chelates are degraded by said culture.

2. The method of claim 1 wherein said aminopolycarboxylic acids are ethylenediaminetetraacetic acid, propylenediaminetetraacetic acid or mixtures thereof.

3. The method of claim 1 wherein said aqueous solution further comprises at least one other source of carbon and/or nitrogen.

4. The method of claim 3 wherein said at least one other source of carbon and/or nitrogen is selected from the group consisting of sucrose and yeast extract.

5. The method of claim 1 wherein basal medium is added to the aqueous solution, said basal medium comprising:
  (i) a salt of ammonium chloride, magnesium sulfate or calcium sulfate;
  (ii) at least one trace mineral salt selected from the group consisting of $H_3BO_3$, $MnSO_4.7H_2O$, $ZnSO_4.7H_2O$, $SuCO_4.H_2O$, $(NH_4)_6MO_7O_{24}.H_2O$, and $CoSO_4.7H_2O$; and
  (iii) biotin.

6. The method of claim 1 wherein the aqueous solution is maintained at a pH of about 8.0 or below.

7. The method of claim 6 wherein a buffer is added to the aqueous solution.

8. The method of claim 7 wherein the buffer is a phosphate buffer.

9. The method of claim 6 wherein an acid is added to the aqueous solution in amounts sufficient to maintain the pH at about 8.0 or less.

10. The method of claim 9 wherein the acid is an inorganic mineral acid.

11. A method of recovering iron from aqueous solutions containing ferric chelates of aminopolycarboxylic acids which method comprises:
  a) adding a biologically pure culture of *Agrobacterium sp.*, ATCC number 55002, to an aqueous solution containing one or more ferric chelates of aminopolycarboxylic acids under conditions suitable for growth of said culture on said chelates;
  b) maintaining the aqueous solution at a pH of about 8 or less at a temperature and for a period of time sufficient for iron to precipitate from solution; and
  c) recovering said iron.

12. A method of degrading ferric chelates of aminopolycarboxylic acids having two or more amino groups and three or more carboxylic acid groups which comprises adding a biologically pure culture of *Agrobacterium sp.*, ATCC number 55002, to a landfill medium containing one or more ferric chelates of aminopolycarboxylic acids under conditions suitable for growth of said culture on said chelates, and maintaining the contact between said chelates and the culture until said chelates are degraded by said culture.

* * * * *